US012458766B2

(12) United States Patent
Mezger

(10) Patent No.: US 12,458,766 B2
(45) Date of Patent: Nov. 4, 2025

(54) INHALER

(71) Applicant: Markus Mezger, Freiberg am Neckar (DE)

(72) Inventor: Markus Mezger, Freiberg am Neckar (DE)

( * ) Notice: Subject to any disclaimer, the term of this patent is extended or adjusted under 35 U.S.C. 154(b) by 768 days.

(21) Appl. No.: 17/785,986

(22) PCT Filed: Dec. 18, 2019

(86) PCT No.: PCT/DE2019/101106
§ 371 (c)(1),
(2) Date: Jun. 16, 2022

(87) PCT Pub. No.: WO2021/121448
PCT Pub. Date: Jun. 24, 2021

(65) Prior Publication Data

US 2023/0017649 A1 Jan. 19, 2023

(51) Int. Cl.
*A61M 15/00* (2006.01)

(52) U.S. Cl.
CPC .... *A61M 15/0003* (2014.02); *A61M 15/0036* (2014.02); *A61M 15/0048* (2014.02); *A61M 15/0075* (2014.02); *A61M 2202/064* (2013.01)

(58) Field of Classification Search
CPC .............. A61M 15/00; A61M 15/0001; A61M 15/0003; A61M 15/0028; A61M 15/003; A61M 15/0031; A61M 15/0033; A61M 15/0035; A61M 15/0036; A61M 15/0038; A61M 15/004; A61M 15/0041; A61M 15/0045; A61M 15/0048; A61M 15/0065; A61M 15/0068; A61M 15/007; A61M 15/0071; A61M 15/0073
See application file for complete search history.

(56) References Cited

U.S. PATENT DOCUMENTS

| | | | | | |
|---|---|---|---|---|---|
| 5,622,166 | A * | 4/1997 | Eisele | A61M 15/0025 | 128/203.15 |
| 5,921,237 | A * | 7/1999 | Eisele | A61M 15/0025 | 128/203.15 |
| 9,561,336 | B2 * | 2/2017 | Smith | A61M 15/0048 | |
| 2002/0170560 | A1 | 11/2002 | Young et al. | | |
| 2009/0194105 | A1 * | 8/2009 | Besseler | A61M 15/0028 | 128/203.15 |
| 2010/0078022 | A1 | 4/2010 | Striebig et al. | | |
| 2010/0126507 | A1 * | 5/2010 | Lulla | A61M 15/0045 | 128/203.15 |

(Continued)

FOREIGN PATENT DOCUMENTS

| | | |
|---|---|---|
| DE | 20 2012 003 962 | 7/2012 |
| WO | 03/061743 | 7/2003 |

(Continued)

*Primary Examiner* — Colin W Stuart
(74) *Attorney, Agent, or Firm* — Gudrun E. Huckett

(57) ABSTRACT

An inhaler for administering powdery dry substances comprises two substance carrying disks (2, 3). Each disk has a cavity filled with a powdery dry substance. The substance carrying disks (2, 3) are rotatably arranged about a common axis of rotation such that the cavities are opposite each other. The inhaler further has an airway (4) having a piercing nozzle (41). The piercing nozzle is disposed between the substance carrying disks (2, 3).

11 Claims, 6 Drawing Sheets

(56) References Cited

U.S. PATENT DOCUMENTS

| | | | | |
|---|---|---|---|---|
| 2010/0307492 A1* | 12/2010 | Fabien | A61M 15/0041 128/203.15 |
| 2011/0186047 A1* | 8/2011 | Lewis | A61M 15/0075 128/203.15 |
| 2011/0271958 A1* | 11/2011 | Sawant | A61M 15/0048 128/203.12 |
| 2016/0175547 A1* | 6/2016 | Nakamura | A61M 15/0016 128/203.15 |

FOREIGN PATENT DOCUMENTS

| | | |
|---|---|---|
| WO | 2005/014089 | 2/2005 |
| WO | 2005/079727 | 9/2005 |
| WO | 2010/036355 | 4/2010 |
| WO | 2011/004287 | 1/2011 |
| WO | 2013/068579 | 5/2013 |

* cited by examiner

INHALER

BACKGROUND OF THE INVENTION

The present invention concerns an inhaler for administering powdery dry substances.

PRIOR ART

In known embodiments, apparatus for administering by inhalation powdery dry substances, e.g. pharmaceutical preparations, are comprised of a generally approximately palm-size device in whose interior the active substances are located, for example, in a coiled blister strip of deep-drawn aluminum foil. For each administration, this strip is moved forward step by step by relative movement of different housing parts, for example, in the form of protective caps or by separate pivot levers, wherein the respective blister cavities that contain the substance are opened and thereby the active substances are released for inhalation.

Also, inhalers are known that employ two coiled blister strips for administration of two different dry substances, for example, of pharmaceutical preparations. Such inhalers are described, for example, in WO 03/061743 A1, in WO 2005/079727 A2, and in WO 2005/014089 A1.

In general, 30 or 60 individual doses are accommodated on such blister strips in order to be able to cover the monthly need of a patient in case of one or two inhalations per day. In case of a dual blister strip inhaler, two different active substances are administered at the same time. Opening of the blister cavities is realized, for example, by stepwise removal of a foil covering the cavities, wherein the cover foil as well as the emptied blister strip are wound up in the inhaler or must be stored in another way. This requires a usually rather complex mechanism and can be mounted only with great expenditure due to the pliable blister strip.

For dual blister strip inhalers, furthermore a complex mechanism with a large number of parts is required in order to be able to administer the active dry substance to the patient. An inhaler which is distributed under the name Ellipta® is comprised of 28 parts, for example.

Moreover, inhalers are known in which in place of the blister strip a generally approximately circular plastic disk with a number of deep-drawn cavities or bores for accommodating the powdery substances is used, wherein the closure of the cavities after their filling is realized by means of a cover foil that is sealed on. For each use of the device, the plastic disk is indexed by one step until all cavities are opened and emptied by inhalation of the powder. For inhalation, the cavities are opened in these devices by a removal element by means of a pushed-in tip and thereby the active substance is released for inhalation. Such an inhaler is disclosed in WO 2013/068579 A1.

Such inhalers contain however only one plastic disk so that they enable only the administration of one substance.

It is an object of the present invention to provide an inhaler that enables the simultaneous administration of two powdery dry substances and can be manufactured more easily than a conventional dual blister strip inhaler. In particular, the inhaler should comprise fewer parts than a conventional dual blister strip inhaler.

SUMMARY OF THE INVENTION

This object is solved by an inhaler for administration of powdery dry substances which comprises two substance carrier disks. Each substance carrier disk comprises cavities filled respectively with a powdery dry substance, preferably at least 30 cavities, respectively. The powdery dry substances can be in particular substances with a particle size in the range of 2 μm to 100 μm. The cavities of the first substance carrier disk are filled in particular with a different powdery dry substance than the cavities of the second substance carrier disk. The substance carrier disks are rotatably arranged about a common axis of rotation such that the cavities are respectively positioned opposite each other. The inhaler comprises moreover an air channel. The air channel comprises a piercing nozzle that is arranged between the substance carrier disks. This arrangement of the air channel, through which a mixture of air and a powdery dry substance can be guided to a mouthpiece of the inhaler, enables a similar spatial distance and a similar geometric position of a removal position from a cavity to be pierced relative to the mouthpiece as this is usually provided in an inhaler with a substance carrier disk. In this way, the same aerodynamic behavior of the dry substance particles in the air flow can be achieved so that similar inhalation parameters as in known inhalers with only one substance carrier disk can be achieved.

In that the powdery dry substance is not stored in blister strips but in substance carrier disks, it is possible to produce the inhaler according to the invention in a simple manner and by utilization of few parts. This leads to a significant cost reduction for the manufacture of the inhaler according to the invention since the parts of the inhaler usually are produced in an injection molding method from thermoplastic plastic materials and for each part to be manufactured a separate injection molding tool must be manufactured.

By rotation of the substance carrier disks, the cavities filled with the powdery dry substance can be brought to face sequentially the piercing nozzle arranged between the substance carrier disks in order to transport the dry substances into the air channel. In order to realize this rotational movement, it is preferred that each substance carrier disk comprises at its circumferential wall surface a cam groove in which a cam groove guide pin engages, respectively. Due to the movement of the respective cam groove guide pin, a rotational movement of a substance carrier disk can then be triggered.

Preferably, the cam grooves and the cam groove guide pins are configured to effect not only a rotational movement of the substance carrier disks but at the same time a linear displacement of the substance carrier disk along the axis of rotation. This can be realized by a suitable shape of the cam groove. A movement of the cam groove guide pins enables then to not only rotate the substance carrier disks to the respective next cavity but at the same time also move them toward the piercing nozzle in order to enable in this way piercing of the cavities by the piercing nozzle. Thus, two movements can be performed at the same time.

Preferably, the substance carrier disks can be rotated in only one direction, respectively. A return movement can be prevented in particular by a suitable shape of the cam grooves. In this manner, it is prevented that cavities that have already been emptied are again brought together with the piercing nozzle.

Furthermore, it is preferred that the cam grooves are configured to limit a number of rotations of their substance carrier disks. This can be realized in particular in that the cam grooves each have a discontinuity. When all cavities of the substance carrier disks have been emptied, it is prevented in this way that upon further rotation of the substance carrier disks it is attempted again to remove a powdery dry substance from a cavity that has already been emptied beforehand.

It is preferred that the inhaler comprises an actuation element which comprises the cam curve guiding pins. The actuation element enables a user of the inhaler to move the substance carrier disks and to thus rotate them farther to the next filled cavities and to pierce these cavities with the piercing nozzle. In that both cam groove guide pins are arranged at the same actuation element, a simultaneous actuation of both substance carrier disks is enabled.

Each cam groove guide pin is arranged preferably at a resilient end of the actuation element. This makes it possible that the cam groove guide pins return resiliently into an initial position after an actuation of the actuation element.

The cam groove guide pins are preferably arranged such to the actuation element that upon actuation of the actuation element they effect a synchronous movement of the two substance carrier disks. When both substance carrier disks rotate at the same time in the same direction and are moved at the same speed toward the piercing nozzle, it is ensured that the dry substances of the two substance carrier disks are mixed in the same manner in the air channel.

The cavities which are arranged in the substance carrier disks are preferably sealed by a cover foil, respectively. In order to enable a simple manufacture of the substance carrier disks, each substance carrier disk preferably has for this purpose a common cover foil that covers simultaneously all cavities of the substance carrier disk. In particular, the cover foil can be an aluminum foil. When the substance carrier disks are moved toward the piercing nozzle, the latter pierces the cover foils and enables thus the access to the dry substance which has been air-tightly sealed up to this point.

The cover foil comprises preferably a thickness in the range of 20 μm to 50 μm in order to enable a simple piercing by means of the piercing nozzle.

The piercing nozzle is preferably designed such that it comprises two hollow nozzles that each have a length of preferably at least 2 mm. Each of the two hollow nozzles is facing in this context one of the substance carrier disks. In this manner, one hollow nozzle can pierce a cavity of one of the substance carrier disks while the other hollow nozzle pierces a cavity of the other substance carrier disk. The dry substances of the two cavities are then transported through the two hollow nozzles, are mixed in the piercing nozzle, and further transported through the air channel.

In order to enable easy piercing of a cover foil, the hollow nozzles are preferably embodied with sharp edges.

Furthermore, the piercing nozzle comprises preferably a plurality of, in particular four, piercing elements. A respective hollow nozzle and a plurality of, in particular two, piercing elements are facing each substance carrier disk are. The piercing elements can pierce or cut further openings into the cover foil in order to enable an inflow of air into the cavities during an inhalation process. Due to the use of a plurality of piercing elements per hollow nozzle, the air guiding action can be realized such that a uniform and complete emptying of the cavities is ensured.

The air channel comprises preferably an outlet nozzle. The latter can be arranged at the end of the air channel positioned opposite to the piercing nozzle and connected with a mouthpiece of the inhaler. When the piercing nozzle has pierced a cavity of both substance carrier disks, respectively, and in this manner has produced a connection to the dry substances stored therein, a user of the inhaler can breathe in through the mouthpiece and in this way generate an air flow through the air channel. Due to this air flow, the dry substances are sucked as powder air mixture completely out of their cavities, are mixed in the piercing nozzle, and released from the outlet nozzle into the respiratory passages of the user.

At the side of a substance carrier disk or of both substance carrier disks facing away from the cavities, a cavity designation, in particular in the form of a numbering, can be provided. Upon rotation of the substance carrier disk, it is then visibly displayed to a user by the cavity designation which cavities are facing the piercing nozzle.

The substance carrier disks can be comprised in particular of a thermoplastic plastic material. The air channel and the piercing nozzle can also be comprised in particular of a thermoplastic plastic material. Particularly preferred, all parts of the inhaler are comprised of a thermoplastic plastic material, respectively. In this way, metal parts can be entirely dispensed with. The plastic parts can be produced, for example, by an injection molding process.

BRIEF DESCRIPTION OF THE DRAWINGS

An embodiment of the invention is illustrated in the drawings and will be explained in more detail in the following description.

PREFERRED EMBODIMENTS

Figure 1:
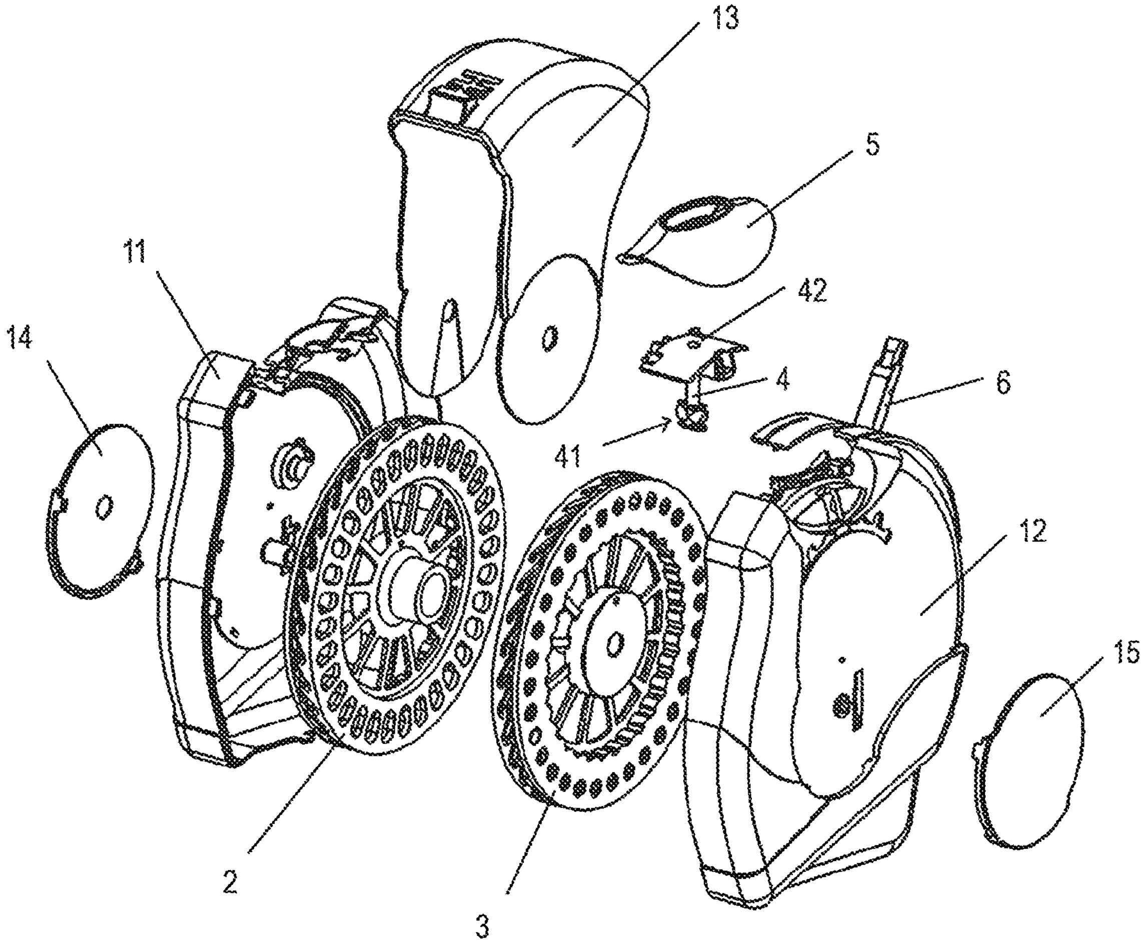
FIG. 1 shows an exploded illustration of an inhaler according to an embodiment of the invention.
Figure 2:
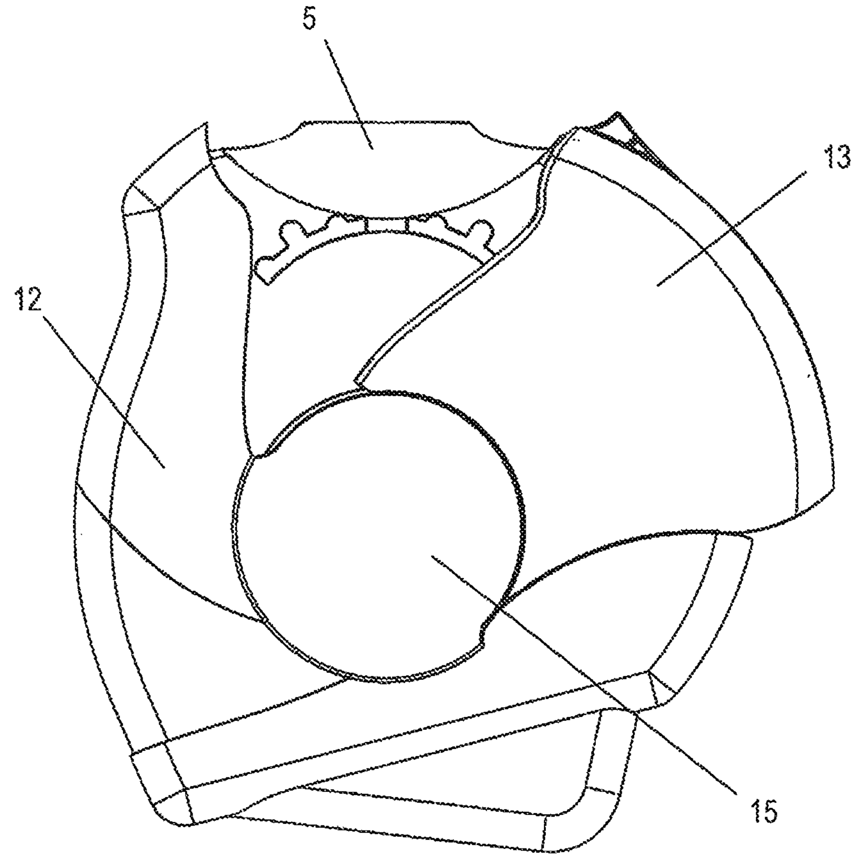
FIG. 2 shows a side view of an inhaler according to an embodiment of the invention.

FIGS. 1 and 2 show an inhaler according to an embodiment of the invention that can be manufactured of only ten parts. They can be produced of a thermoplastic plastic material in an injection molding process. The housing of the inhaler is comprised of a first housing half 11 and a second housing half 12. When they are assembled, a cover 13 is attached to the two housing halves 11, 12 such that it encloses them. A first lid 14 is attached from the side of the first housing half 11 onto the cover 13. A second lid 15 is attached from the side of the second housing half 12 onto the cover 13. In this way, the cover 13 is fixed on the two housing halves 11, 12.

In the housing, a first substance carrier disk 2 and a second substance carrier disk 3 are arranged. They are arranged rotatably on a common axis of rotation about which also the cover 13 is pivotable. An air channel 4 that comprises a piercing nozzle 41 and an outlet nozzle 42 is arranged in the housing such that the piercing nozzle 41 is positioned between the cavities of the two substance carrier disks 2, 3. The outlet nozzle 42 which is arranged at the end of the air channel 4 facing away from the piercing nozzle 41 faces an opening in the housing. A mouthpiece 5 is attached to this opening.

Figure 3:
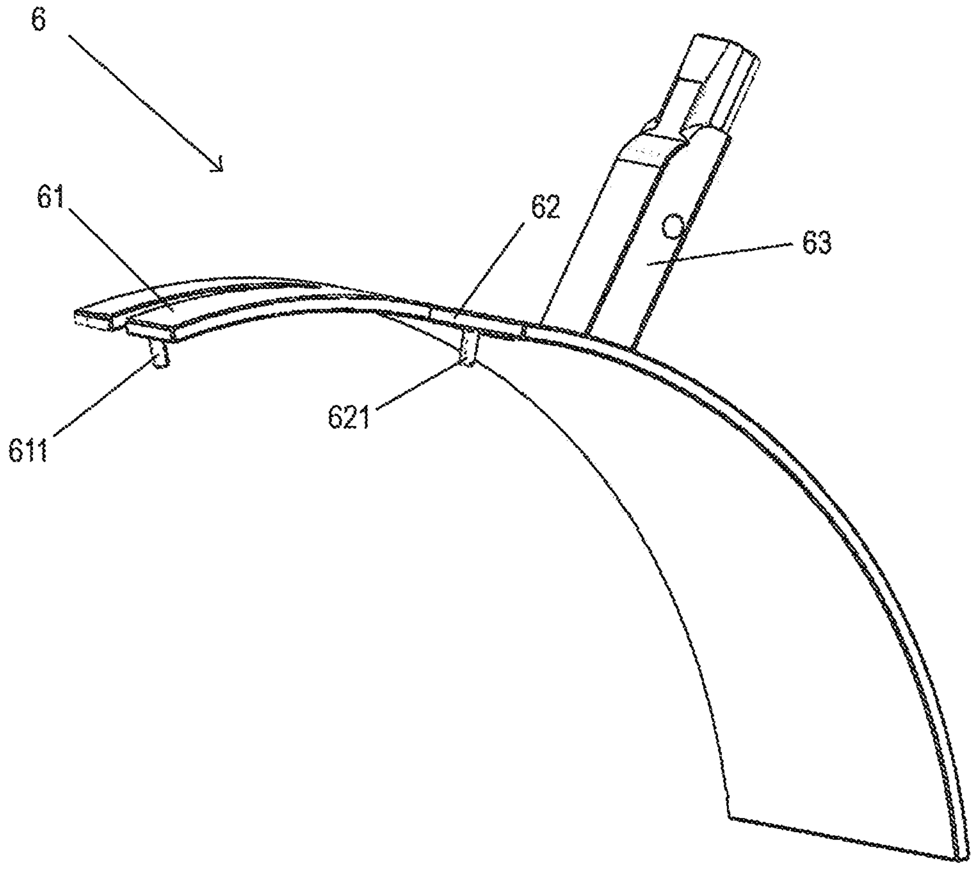
FIG. 3 shows in isometric illustration of an actuation element of an inhaler according to an embodiment of the invention.

An actuation element 6 is arranged in such a way in the inhaler that it is contacting both housing halves 11, 12. As illustrated in FIG. 3, it is of a circular arc shape and comprises two resilient ends 61, 62 that are separated by a gap from each other and extend parallel. At each resilient end 61, 62, a cam groove guide pin 611, 621 is arranged, respectively, in such a way that it projects into the housing. In this context, the first cam groove guide pin 611 engages a first cam groove at the circumferential wall surface of the first substance carrier disk 2 and the second cam groove guide pin 621 engages a second cam groove at the circumferential wall surface of the second substance carrier disk 3. While the cam groove guide pins 611, 621 project into the interior of the circular segment formed by the actuation element 6, a connection element 63 projects from the circular segment to the exterior. It engages from the interior in a receptacle of the cover 13 provided for this purpose. When a user rotates the cover 13 about the common axis of rotation, he moves in doing so also the two cam groove guide pins 611, 621 about the common axis of rotation. This movement is transmitted onto the two substance carrier disks 2, 3.

Figure 4:
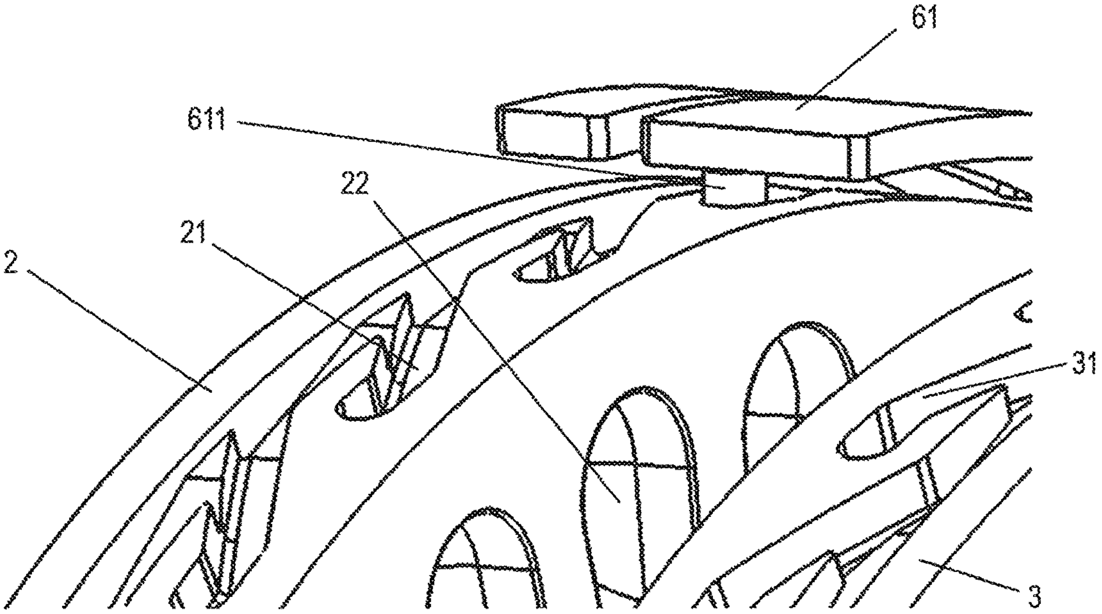
FIG. 4 shows in isometric detail view how a cam groove guide pin engages in a cam groove of a substance carrier disk of an inhaler according to an embodiment of the invention.

FIG. 4 shows the first cam groove 21 of the first substance carrier disk 2 and the second cam groove 31 of the second substance carrier disk 3. Moreover, it is illustrated how the first cam groove guide pin 611 engages the first cam groove 21. The grooves of the first cam groove 21 are shaped such that the first cam groove guide pin 611 in a rest position is resting in a groove of the first cam groove 21 formed by an undercut. When the first cam groove guide pin 611 is now moved along the axis of rotation, it glides along a slant in the first cam groove 21 and pushes the first substance carrier disk 2 in this way along the axis of rotation toward the piercing nozzle 41. After this slant has been overcome, the cam groove guide pin is continued to be guided in the next groove of the cam groove. As soon as it engages it, the first substance carrier disk 2 returns along the axis of rotation into its initial position. When the user now releases the cover 13, the actuation element 6 springs back into its initial position, exerts in doing so pressure against the groove in rotational direction of the first substance carrier disk 2, and rotates the first substance carrier disk 2 thereby farther by one groove. The first cam groove 21 is designed such that one cam groove is provided, respectively, for each cavity in the first substance carrier disk 2. Due to the rotational movement, the first substance carrier disk 2 is therefore rotated farther by one cavity. A symmetric movement along the axis of rotation and a symmetric rotation in the same rotational direction is triggered simultaneously by the second cam groove guide pin 621 in interaction with the second cam groove 31 at the second substance carrier disk 3.

The connection between cover 13 and the actuation element 6 is realized in this context such that the cover 13 in the rest position of the actuation element 6 covers the mouthpiece 5 and protects it in this way from contaminants.

Figure 5:
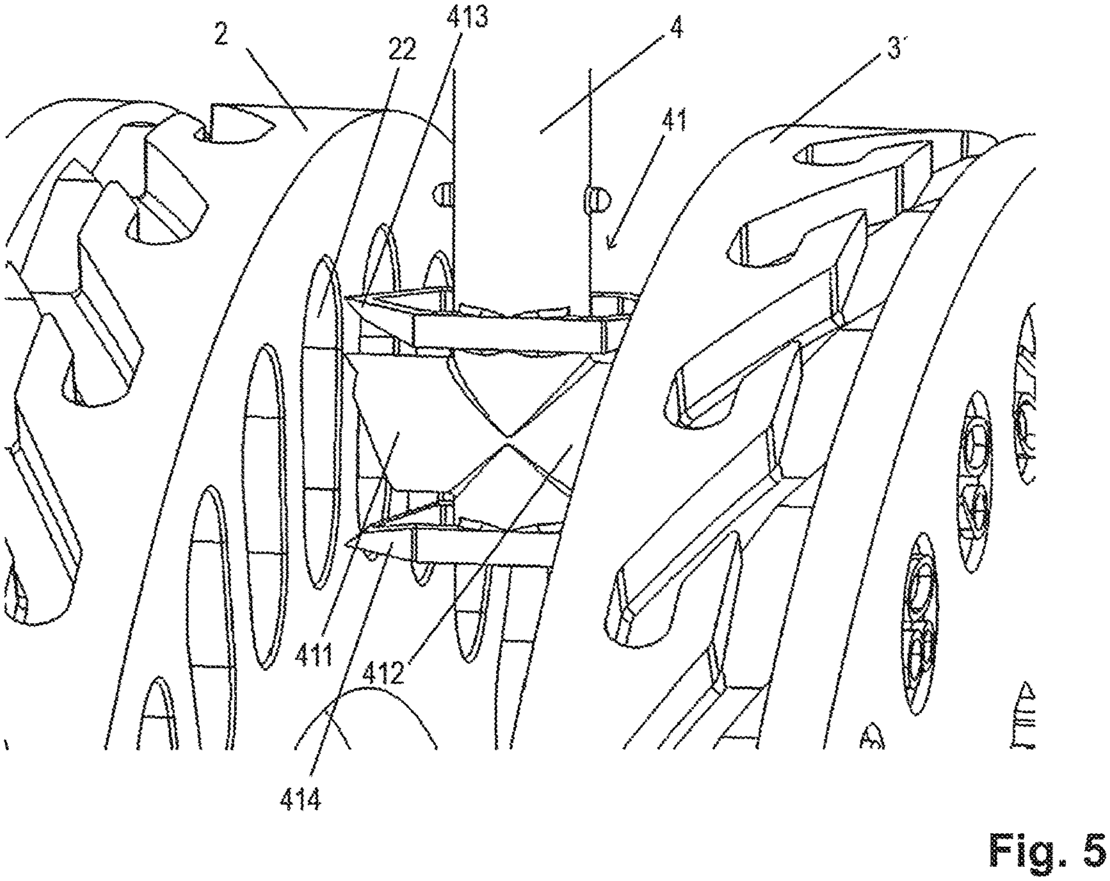
FIG. 5 shows in an isometric detail view the arrangement of a piercing nozzle relative to cavities in the substance carrier disks of an inhaler according to an embodiment of the invention.

FIG. 5 shows how the piercing nozzle 41 is arranged relative to the two substance carrier disks 2, 3. The piercing nozzle 41 comprises two hollow nozzles 411, 412 that are embodied with sharp edges and are positioned orthogonally in relation to the air channel 4. The first hollow nozzle 411 is facing a cavity 22 of the first substance carrier disk 2. The second hollow nozzle 412 is facing a cavity of the second substance carrier disk 3 which is not visible in the view of FIG. 5. Above the first hollow nozzle, a first piercing element 413 is facing the cavity 22 of the first substance carrier disk 2 and, below the first hollow nozzle, a second piercing element 414 faces the cavity 22 of the first substance carrier disk 2. Above and below the second hollow nozzle, a piercing element is also arranged, respectively, that is respectively facing the cavity of the second substance carrier disk 3 that is not visible.

Figure 6:
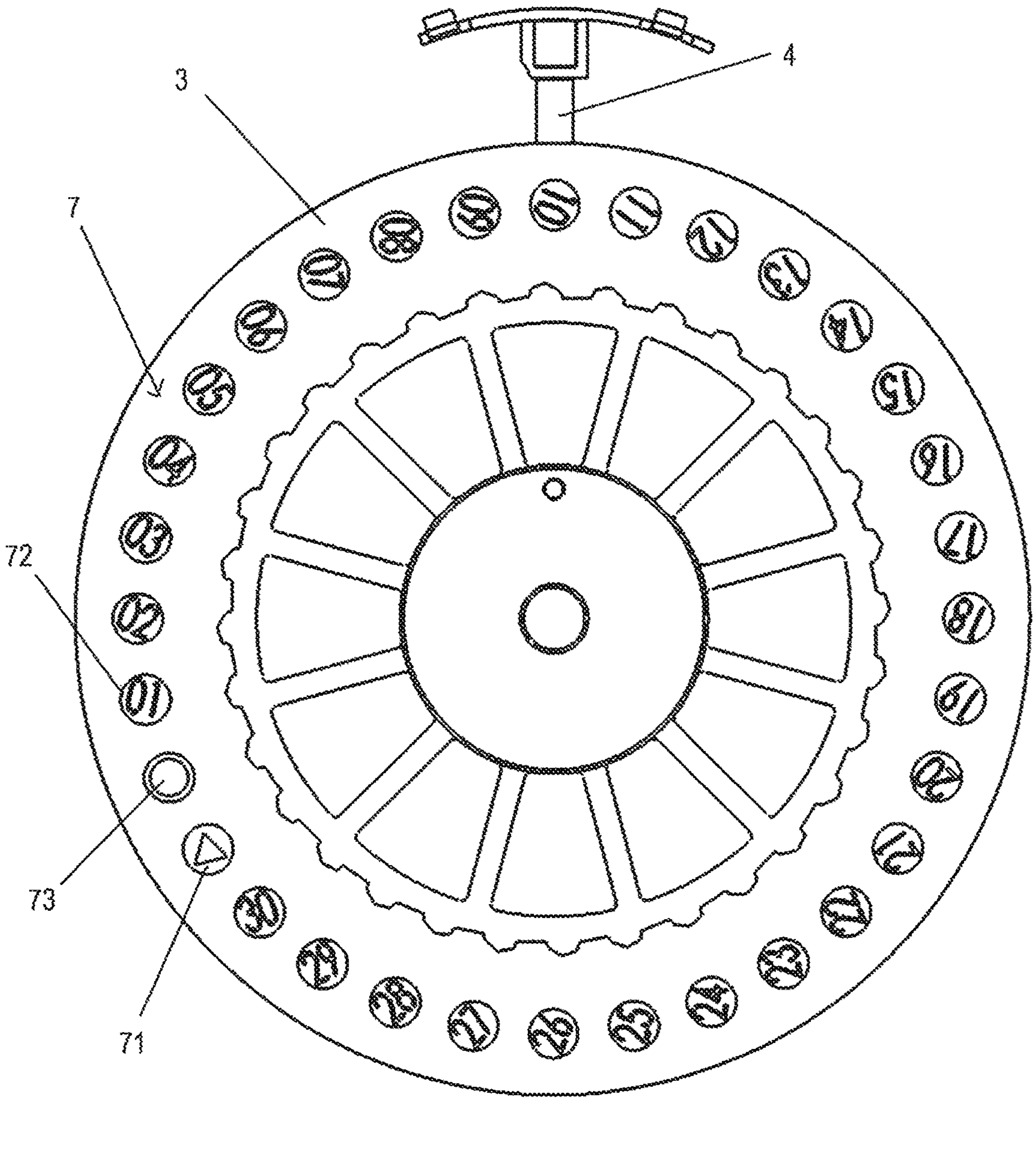
FIG. 6 shows a side view of a substance carrier disk of an inhaler according to an embodiment of the invention.

As illustrated in FIG. 6, the second substance carrier disk 3 at its exterior side that is facing away from its cavities has a cavity designation 7. It begins with the start cavity designation 71 that indicates a first empty cavity. The first empty cavity can be used as a testing cavity in order to test after manufacture of the inhaler its proper function by a first actuation of the actuation element 6. Then active ingredient cavity designations 72, numbered from 30 to 1, follow for the cavities which contain respectively an active ingredient in the form of a powdery dry substance. Following the last active ingredient cavity designation 72 identified by No. 1, an end cavity designation 73 follows. It characterizes also an empty last cavity of the second substance carrier disk 3. The second cam groove 31 comprises between the cavity with the start cavity designation 71 and the cavity with the end cavity designation 73 a discontinuity so that a further rotation of the second substance carrier disk 3 is not possible. Through an opening in the second housing half 12, a user of the inhaler can recognize the active ingredient cavity designation of the respective actual cavity.

Figure 7:
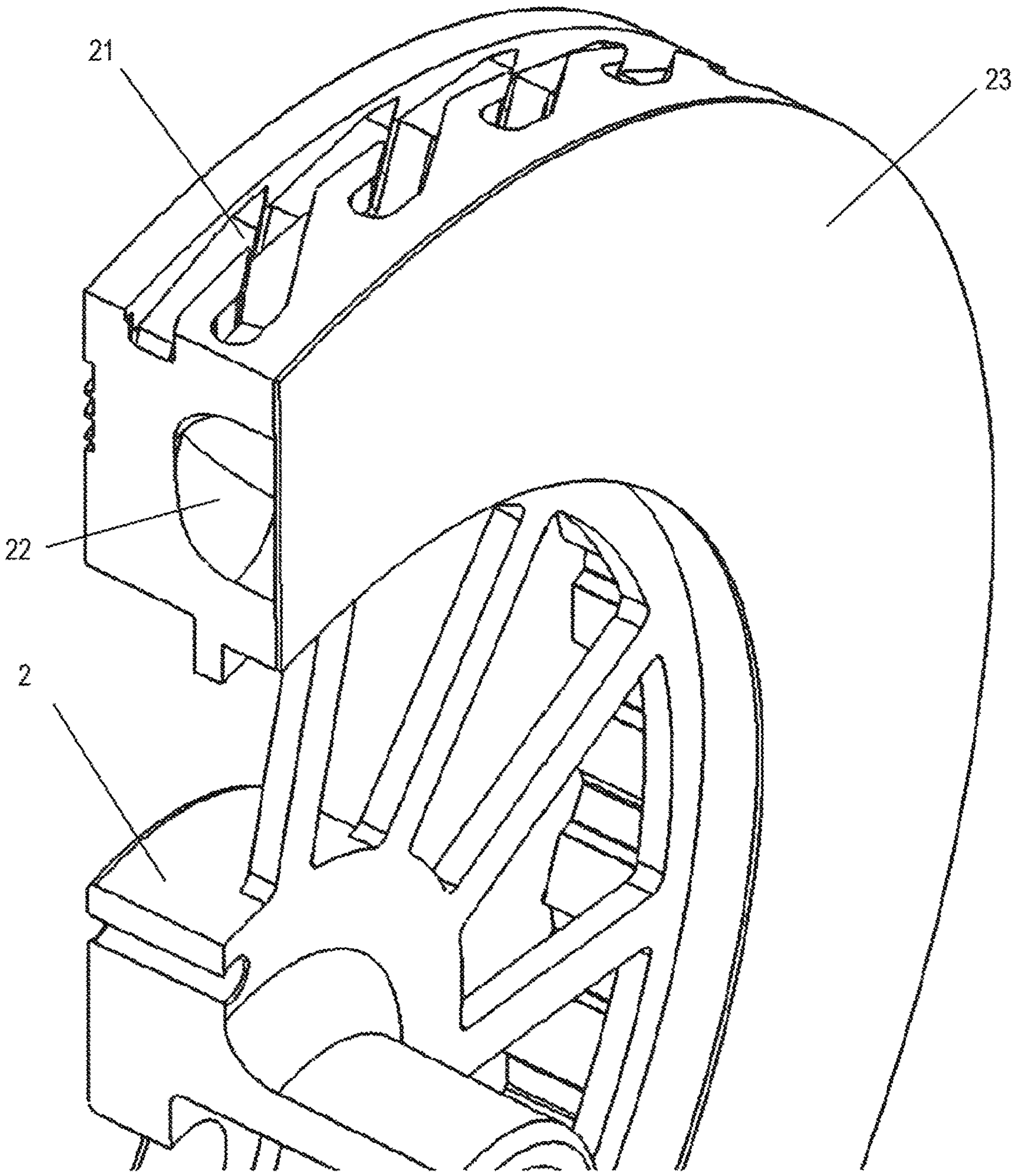
FIG. 7 shows in isometric section illustration a substance carrier disk in an inhaler according to an embodiment of the invention that comprises a cover foil.

The cavities in FIGS. 1, 4, and 5 are illustrated without cover for ease of understanding. Actually, they each comprise a cover foil, respectively. In FIG. 7, the cover foil 23 of the cavities 22 of the first substance carrier disk is illustrated. It is here an aluminum foil. The latter ensures that the powdery dry substances in the interior of the cavities 22 are closed air-tightly. When the two substance carrier disks 2, 3 are moved toward the piercing nozzle 41, the two hollow nozzles 411, 412 cut with their sharp edges the cover foil 23 of the first substance carrier disk as well as the cover foil of the second substance carrier disk and open thus a connection between the respective cavities and the piercing nozzle 41. Also, the piercing elements 413, 414 cut further openings into the cover foil and enable thus inflow of air into the cavities. This enables a user who breathes in through the mouthpiece 5 to inhale the powdery dry substances from the cavities through the piercing nozzle 41, the air channel 4, and the outlet nozzle 42 whereby they are finally dispersed. Air flows above and below the hollow nozzles 411, 412, respectively, into the cavities so that the cavities can be uniformly and completely emptied.

LIST OF REFERENCE CHARACTERS

11: first housing half
12: second housing half
13: cover
14: first lid
15: second lid
2: first substance carrier disk
21: first cam groove
22: cavity
23: cover foil
3: second substance carrier disk
31: second cam groove
4: air channel
41: piercing nozzle
411: first hollow nozzle
412: second hollow nozzle
413: first piercing element

414: second piercing element
42: outlet nozzle
5: mouthpiece
6: actuation element
61: first resilient end
611: first cam groove guide pin
62: second resilient end
621: second cam groove guide pin
63: connection element
7: cavity designation
71: start cavity designation
72: test cavity designation
73: active ingredient cavity designation

What is claimed is:

1. An inhaler for administration of a powdery dry substance, the inhaler comprising:

a first substance carrier disk comprising first cavities filled with the powdery dry substance and a second substance carrier disk comprising second cavities filled with the powdery dry substance;

wherein the first and the second substance carrier disks are rotatably arranged about a common axis of rotation;

wherein the first cavities are positioned opposite the second cavities, respectively;

an air channel comprising a piercing nozzle arranged between the first and the second substance carrier disks.

2. The inhaler according to claim 1, wherein the first substance carrier disk comprises a first circumferential wall surface and a first cam groove arranged at the first circumferential wall surface, wherein the second substance carrier disk comprises a second circumferential wall surface and a second cam groove arranged at the second circumferential wall surface, wherein a first cam groove guide pin engages the first cam groove, and wherein a second cam groove guide pin engages the second cam groove.

3. The inhaler according to claim 2, wherein the first cam groove and the first cam groove guide pin are configured to effect a linear displacement of the first substance carrier disk along the common axis of rotation and a rotational movement of the first substance carrier disk, and wherein the second cam groove and the second cam groove guide pin are configured to effect a linear displacement of the second substance carrier disk along the common axis of rotation and a rotational movement of the second substance carrier disk.

4. The inhaler according to claim 2, wherein the first cam groove is configured to limit a number of rotations of the first substance carrier disk, and wherein the second cam groove is configured to limit a number of rotations of the second substance carrier disk.

5. The inhaler according to claim 2, further comprising an actuation element, wherein the actuation element comprises the first and the second cam groove guide pins.

6. The inhaler according to claim 5, wherein the first and the second cam groove guide pins are arranged at a resilient end of the actuation element, respectively.

7. The inhaler according to claim 5, wherein the first and the second cam groove guide pins are arranged at the actuation element such that the first and the second cam groove guide pins effect a synchronous movement of the first and the second substance carrier disks upon actuation of the actuation element.

8. The inhaler according to claim 1, further comprising a first cover foil sealing the first cavities at the first substance carrier disk and a second cover foil sealing the second cavities at the second substance carrier disk.

9. The inhaler according to claim 1, wherein the piercing nozzle comprises a first hollow nozzle and a second hollow nozzle, wherein the first hollow nozzle is facing the first substance carrier disk and the second hollow nozzle is facing the second substance carrier disk.

10. The inhaler according to claim 9, wherein the piercing nozzle comprises first piercing elements and second piercing elements, wherein the first hollow nozzle and the first piercing elements are facing the first substance carrier disk, and wherein the second hollow nozzle and the second piercing elements are facing the second substance carrier disk.

11. The inhaler according to claim 1, further comprising a mouthpiece, wherein the air channel comprises an outlet nozzle, and wherein the outlet nozzle is connected to the mouthpiece.

* * * * *